United States Patent
Niemeyer, III (10) Patent No.: US 9,310,283 B2
(45) Date of Patent: Apr. 12, 2016

(54) GOLF BALL COMPRESSION TESTER

(75) Inventor: Robert Henry Niemeyer, III, Tigard, OH (US)

(73) Assignee: Compression Matters Corporation, Las Vegas, NV (US)

(*) Notice: Subject to any disclaimer, the term of this patent is extended or adjusted under 35 U.S.C. 154(b) by 857 days.

(21) Appl. No.: 13/312,617

(22) Filed: Dec. 6, 2011

(65) Prior Publication Data

US 2012/0166106 A1 Jun. 28, 2012

Related U.S. Application Data

(60) Provisional application No. 61/459,060, filed on Dec. 6, 2010.

(51) Int. Cl.

| | |
|---|---|
| *G01B 21/06* | (2006.01) |
| *G01N 3/08* | (2006.01) |
| *A63B 47/00* | (2006.01) |
| *G01N 3/40* | (2006.01) |
| *A63B 37/00* | (2006.01) |
| *G01N 33/00* | (2006.01) |

(52) U.S. Cl.
CPC ............... *G01N 3/08* (2013.01); *A63B 37/0087* (2013.01); *A63B 47/008* (2013.01); *G01N 3/40* (2013.01); *A63B 37/0003* (2013.01); *A63B 37/0004* (2013.01); *A63B 2220/17* (2013.01); *A63B 2220/20* (2013.01); *A63B 2220/56* (2013.01); *G01N 2033/0078* (2013.01); *G01N 2203/0085* (2013.01); *G01N 2203/0276* (2013.01); *G01N 2203/0482* (2013.01)

(58) Field of Classification Search
CPC ..... G01C 22/006; G01C 15/002; G01C 15/008
USPC ................................................... 702/160, 163
See application file for complete search history.

(56) References Cited

U.S. PATENT DOCUMENTS

| 2,278,416 | A | * | 4/1942 | Atti ................................ 73/818 |
| 2,694,535 | A | | 11/1954 | Atti |
| 3,665,757 | A | | 5/1972 | Hoag |
| 4,555,028 | A | | 11/1985 | Valehrach |
| 6,196,073 | B1 | * | 3/2001 | Harding .................. 73/862.381 |
| 6,755,085 | B1 | | 6/2004 | Kazanjian et al. |
| 6,804,988 | B2 | | 10/2004 | McNamara et al. |

(Continued)

OTHER PUBLICATIONS

Chapter 3: Basic Definitions of Stress and Strain, Mechanical Properties of Engineered Materials, 2003 Marcel Dekker.*

(Continued)

*Primary Examiner* — Michael Nghiem
*Assistant Examiner* — Robert Dewitty
(74) *Attorney, Agent, or Firm* — Fellers, Snider, Blankenship Bailey & Tippins, P.C.

(57) ABSTRACT

A device for measuring the spring rate of a golf ball is disclosed. The device receives a golf ball between a first anvil and a second anvil. A force gauge is provided on one anvil. A displacer is provided on another anvil. Each anvil defines a ball receiving depression that is larger than the dimples of the golf ball to be measured for negating measurement effects due to golf ball dimples when measurement of the golf ball is conducted. The displacement an anvil is determined. From the force data and displacement data, a spring rate of the golf ball can be calculated and a compression scale value may be calculate and displayed on the device for informing a golfer that is operating the hand held device.

20 Claims, 10 Drawing Sheets

(56) References Cited

U.S. PATENT DOCUMENTS

| | | |
|---|---|---|
| 7,777,871 B2 | 8/2010 | McNamara et al. |
| 2005/0066741 A1 | 3/2005 | O'Brien et al. |
| 2009/0120201 A1 | 5/2009 | Mendoza |

OTHER PUBLICATIONS

KIPO, International Search Report and Written Opinion for PCT/US2011/063550, Jul. 20, 2012, Publisher: Korean Intellectual Property Office.

* cited by examiner

GOLF BALL COMPRESSION TESTER

CROSS REFERENCE TO RELATED APPLICATIONS

This application claims the priority of U.S. Provisional Patent Application No. 61/459,060, entitled "GOLF BALL COMPRESSION TESTER," filed Dec. 6, 2010, the contents of which are hereby incorporated by reference.

FIELD OF THE INVENTION

This invention relates to a device that is used to find a "compression rating" of a golf ball. More particularly, the invention relates to a portable handheld device that may be used to find a compression rating of a golf ball by a golfer while golfing on a golf course.

BACKGROUND OF THE INVENTION

Golf balls are manufactured having a variety of properties for appealing to a wide range of golfers. One characteristic of a golf ball is the "compression rating" or compression scale value. The compression rating, at one time in the past, was a measurement of how tightly the rubber threads of the ball were wound around a core of the ball. The tighter the rubber threads, the high the compression rating or the higher the hardness of the ball. Modern manufacturing techniques have replaced the winding of rubber threads with solid rubber, thereby necessitating a way to relate the familiar compression rating of wound balls to solid balls. Some golf ball manufacturers have stopped using the compression rating altogether. Consequently, golfers may benefit from a way to measure a ball to determine what the compression rating of a ball is.

Generally, golf balls having a lower compression rating are favored by golfers having a slower swing speed, while golf balls having a higher compression rating are favored by golfers having a faster swing speed. Golf balls are available in a variety of compression ratings, most commonly designated by a compression scale that is expressed in a value that ranges from 50 to 120. Low compression balls, e.g., balls having a compression rating of 70 or below, rebound off the club head differently than high compression balls, e.g., ball having compression ratings of 100 or above. Medium compression balls, e.g., balls having a compression rating of approximately 90, rebound differently than high or low compression rated balls. Knowing the characteristics of the golf ball will allow a golfer to choose the ball that best matches his swinging speed.

SUMMARY OF THE INVENTION

A device is provided for measuring the compression rating of a golf ball. The device has a housing that defines a ball receiving receptacle for receiving a golf ball. A first anvil and a second anvil are mounted in the housing for receiving the golf ball there between. A force gauge is provided that is in communication with one of the first anvil and the second anvil, preferably with the upper anvil. A displacer, such as a threaded rod, is in communication with one of the first anvil and the second anvil, preferably with the lower anvil.

The first anvil defines a first ball receiving surface that defines a first ball receiving depression. The second anvil defines a second ball receiving surface that defines a second ball receiving depression. The first ball receiving depression and the second ball receiving depression are larger than the dimples of the golf ball to be measured for negating measurement effects due to golf ball dimples when measurement of the golf ball is conducted. The displacement of one of the first anvil and the second anvil, preferably the lower anvil, is determined. From the force data and displacement data, a spring rate of the golf ball can be determined and a compression scale value displayed on the device for informing a golfer that is operating the hand held device.

In use, a golf ball is located between the first anvil and the second anvil in depressions defined by the anvil surfaces. The golf ball is compressed by displacing one of the first anvil and the second anvil, preferably the lower anvil, to produce a deflection of the golf ball. A displacement of the one of the first anvil and the second anvil, preferably the lower anvil, is determined and communicated to a processor. A force delivered to the one of the first anvil and the second anvil, preferably the upper anvil, as a result of compressing the golf ball is determined. The force is communicated to the processor. The spring rate is calculated by the processor by dividing the force by the deflection of the golf ball. The spring rate is then converted to a compression scale value, e.g., 50 to 120, and is then displayed on a display screen for viewing by a golfer.

An object of this invention is to provide a hand-held device that will measure the spring rate of a golf ball to a very high degree of accuracy and repeatability.

A further object of this invention is to provide a way to relate a measured spring rate of a golf ball to a compression scale value that a majority of people familiar to the game of golf have used and understood for many years.

A further object of the invention is to display a compression scale value so a person familiar with the game of golf will be able to relate a golf ball hardness to a performance of the ball and to performance of the golfer.

A further object of this invention is to provide a measuring tool that is compact and lightweight enough to be carried while playing a game of golf.

A further object of this invention is to provide a device that measures the spring rate of a golf ball to a set of absolute standards.

A further object of the invention is to measure the spring rate of a golf ball to such a high degree of accuracy that the device of the invention can be used to check the quality of manufacturing of the golf ball and verify that the ball meets an advertised compression rating.

A further object of this invention is to provide a device that can verify that a golf ball meets or exceeds compression rating standards that have been established by organizations such as the Professional Golf Association, hereafter known as the "PGA".

A further object of this invention is to measure the spring rate of a golf ball without causing damage to the golf ball, such as causing the ball to be out of roundness or marking the surface of the ball.

A further object of this invention is to related how a temperature of a ball can change the compression scale value of the ball.

BRIEF DESCRIPTION OF THE DRAWINGS

The foregoing and other objects of this invention will become more fully apparent from the following detailed description of an embodiment of the invention and from the accompanying drawings, in which.

DETAILED DESCRIPTION OF THE PREFERRED EMBODIMENTS

Figure 1:
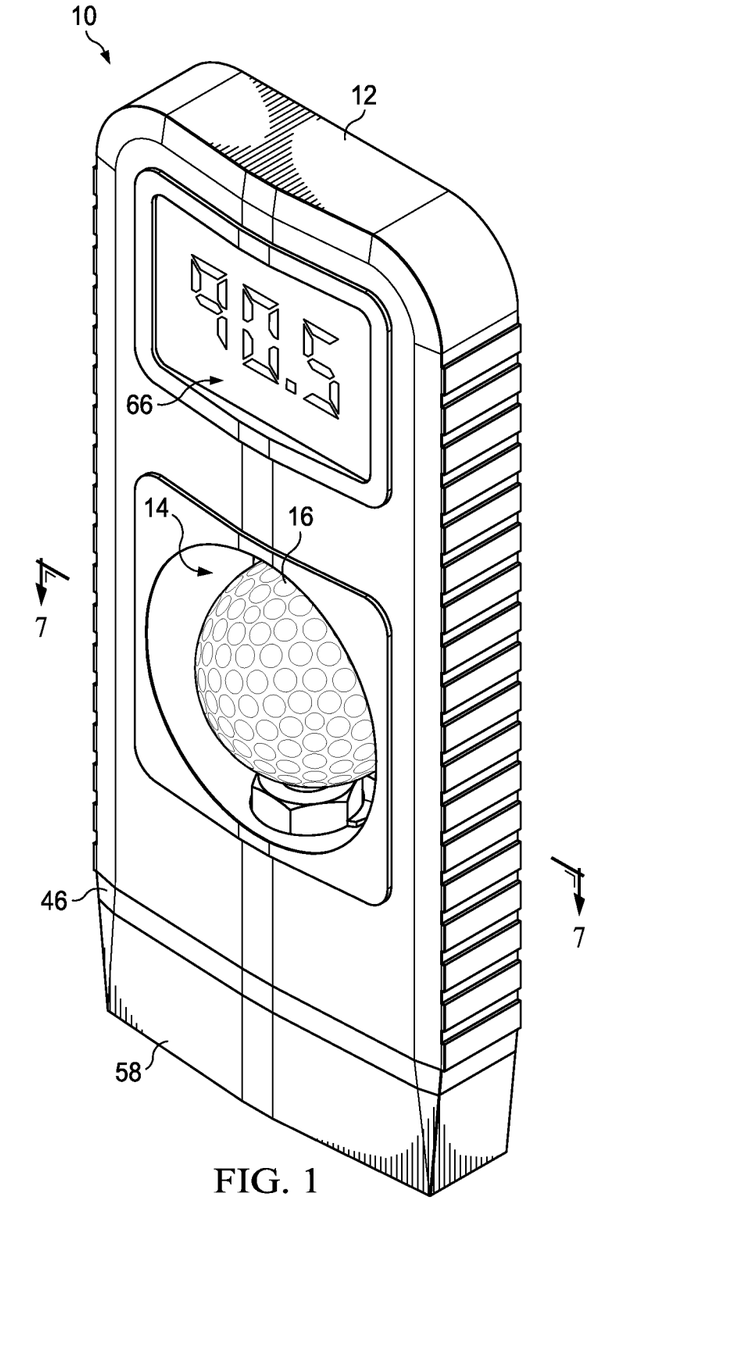
FIG. 1 is an isometric view of a golf ball compression tester device of the invention.
Figure 4:
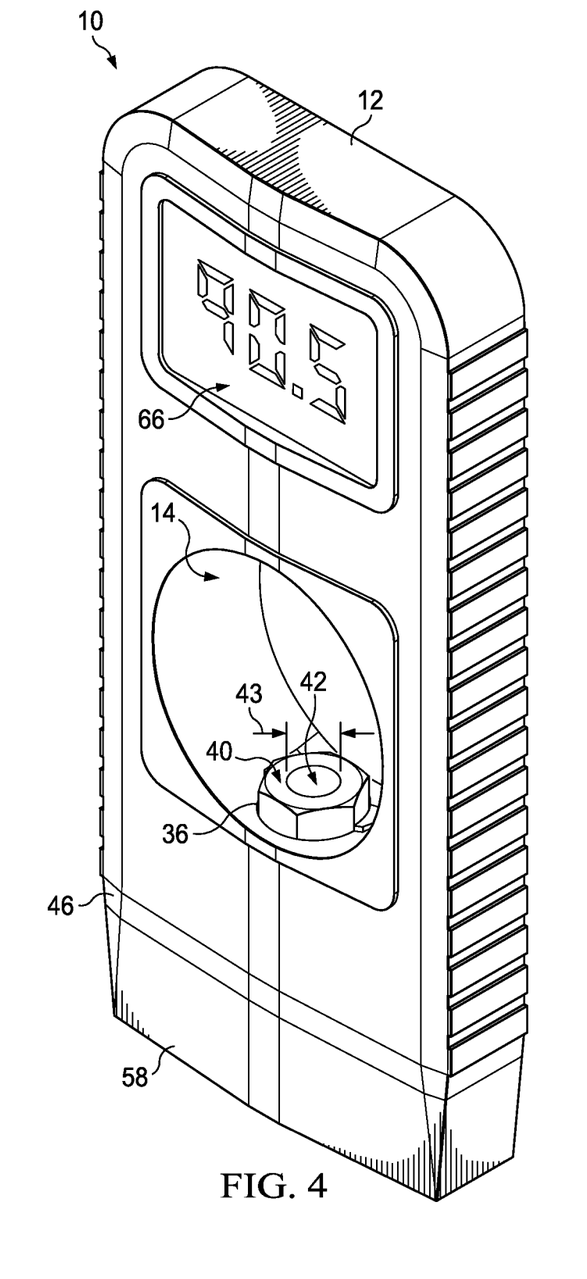
FIG. 4 is an isometric view of the device of FIG. 1 showing a recessed area of a lower anvil provided for "dimple negation".

Referring now to the figures, shown is a golf ball compression testing device, designated generally 10. Device 10 includes a housing 12 that defines a ball receiving receptacle 14 for receiving a golf ball 16 to be tested. Device 10 includes a force gauge assembly 18 located in housing 12. Force gauge assembly 18 includes an upper anvil 20 (FIGS. 1, 4, 5) secured in an upper anvil housing 22 by retaining ring 23. Housing 22 preferably has a hexagonal shape for preventing rotation, but other shapes may also be utilized. Upper anvil 20 defines an upper ball receiving surface 24 on a lower side that defines an upper depression 26 having a diameter 27. Upper anvil 20 defines a protuberance 28 on an upper surface that selectively communicates with beam 30 of a tension measuring device 32 (FIGS. 2, 4, 5), e.g., a strain gauge, for measuring a force applied by protuberance 28 of upper anvil 20. Strain gauges are useful to get very high degrees of accuracy and repeatability for measuring applied forces without also requiring a significant ball deflection due to forces that would complicate the measurement taken.

Figure 2:
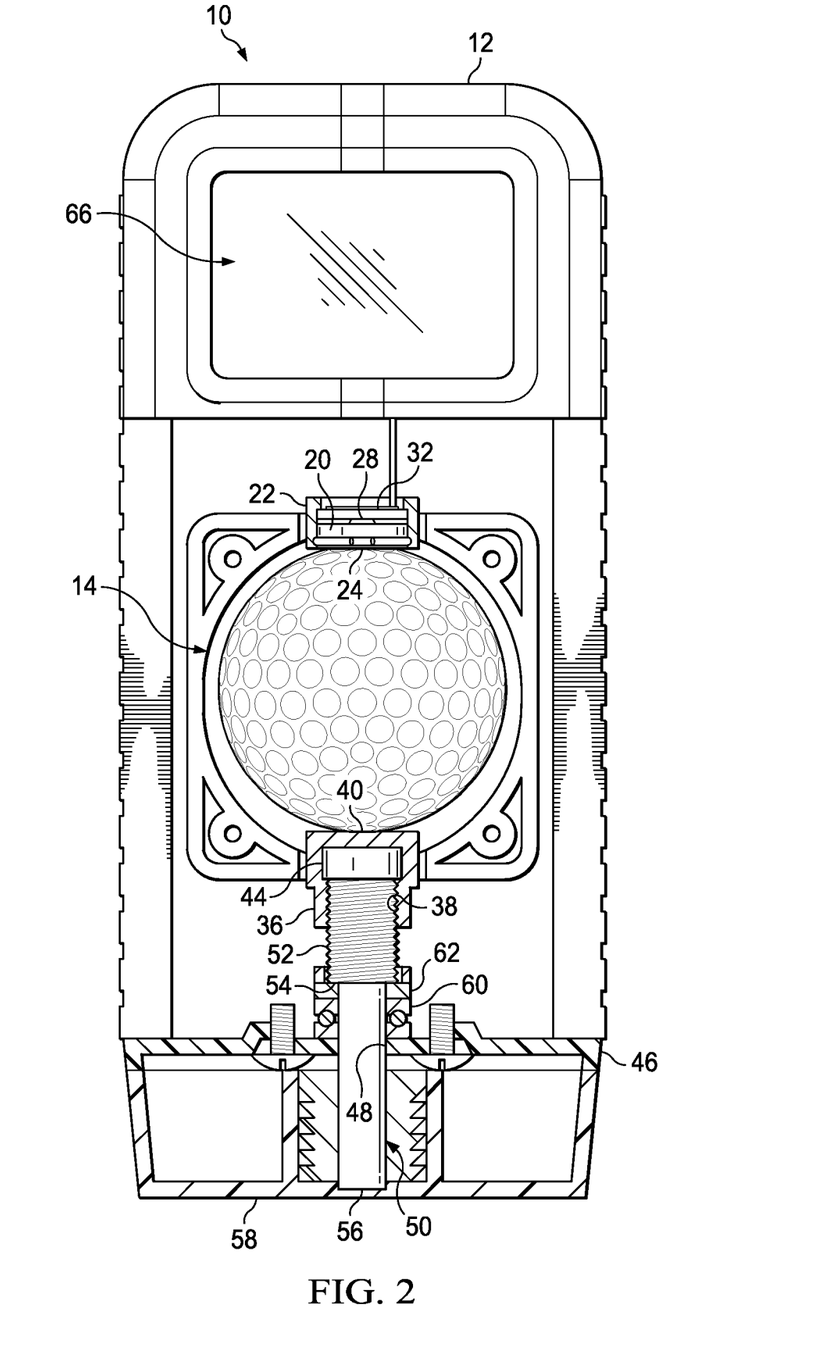
FIG. 2 is an isometric partial cut-away view showing the internal mechanics of the golf ball compression tester of FIG. 1.

Force gauge assembly 18 additionally includes a lower anvil 36. Lower anvil 36 defines internal threads 38. Lower anvil 36 is preferably hexagonally shaped to prevent rotation when handle 58 is rotated to compress ball 16, as will be explained below. Lower anvil 36 has an upper surface that defines a lower ball receiving surface 40. Lower ball receiving surface 40 defines a lower depression 42 having a diameter 43. Lower anvil 36 may have a lower surface that communicates with thrust member 44, as shown in FIG. 2.

Bottom plate 46 is affixed to a lower end of housing 12. Bottom plate 46 defines central orifice 48. A displacement mechanism, such as threaded rod 50, extends through central orifice 48 of bottom plate 46. Threaded rod 50 defines an upper threaded end 52 that is threadably received within internal threads 38 of lower anvil 36. Upper threaded end 52 of threaded rod 50 may contact a lower surface of thrust member 44 (FIG. 2). Upper threaded end 52 preferably defines left handed Acme threads having a known thread pitch. The thread pitch is a trade-off between the number of turns required to make a measurement and the amount of torque required to turn the handle to make a measurement.

Figure 3:
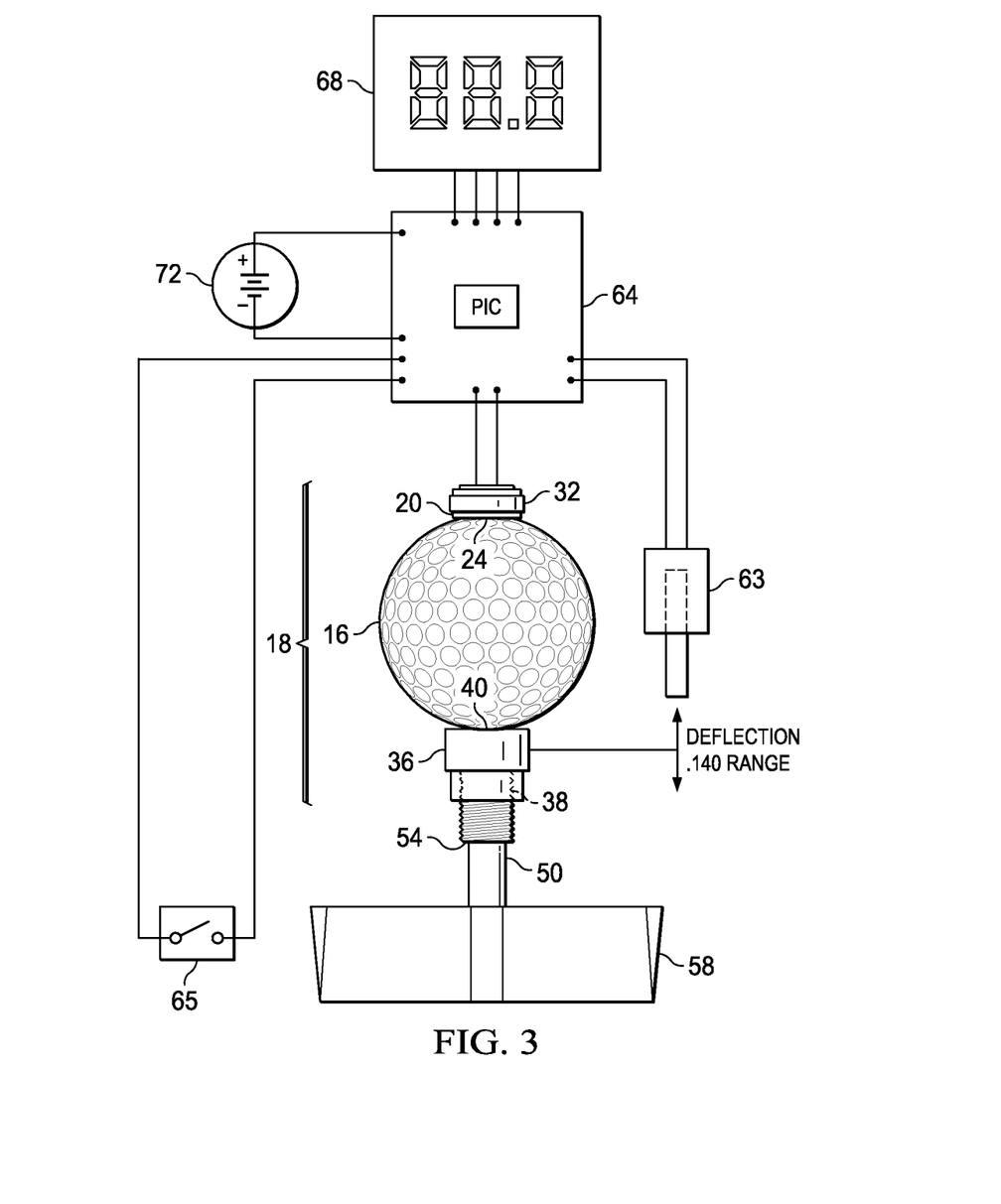
FIG. 3 is a schematic view of one embodiment of sensing components of the device of FIG. 1.

The preferred thread pitch is ⅟16 inch. Threaded rod 50 additionally defines a downwardly facing shoulder 54 (FIGS. 2, 3). Threaded rod 50 has a lower end 56 that extends outwardly from bottom plate 46.

Handle 58 is affixed to lower end 56 of threaded rod 50 for rotating threaded rod 50 to induce axial displacement of lower anvil 36. Thrust bearing 60 surrounds threaded rod 50 and is located between downwardly facing shoulder 54 and an upper surface of bottom plate 46. Thrust bearing 60 is provided to take the force applied against ball 16. Thrust bearing 60 decreases the torque needed to rotate handle 14 to compress ball 16 with lower anvil 36. Alternatively, threaded rod 58 may be rotated by a motor (not shown).

Encoder wheel 62 is located between an upper surface of thrust bearing 60 and downwardly facing shoulder 54 of threaded rod 50. Encoder wheel 62 is provided to mechanically or electrically track a number of rotations of threaded rod 50. The rotation tracking is converted into deflection by using a relationship of threads or threaded end 52 to a reading from encoder wheel 62. Encoder wheel 62 may be optical, magnetic, or use other means of tracking a number of rotations of threaded rod 50. Alternatively, deflection may be sensed by a deflection gauge 63. In a preferred embodiment, maximum deflection is 0.140", although other ranges may be used.

Processor 64 is provided within housing 12 and communicates with encoder wheel 62 for converting the number of rotations of threaded rod 50 and the known thread pitch into a measurement of axial displacement of lower anvil 36. Alternatively, processor 64 communicates with deflection gauge 63 (FIG. 3). Processor 64 is additionally in communication with tension measuring device 32. Switch 65 is also in communication with processor 64 and may be manual or automatic as is discussed below.

A display assembly 66 (FIG. 9) is provided in housing 12. Display assembly 66 includes front bezel 67, display panel 68, such as an LCD, processor 64 and a zebra strip 69 interposed between processor 64 and display panel 68. A back bezel 70 engages a rear surface of housing 12 and receives battery door 71 for securing a power supply, such as a lithium battery 72, in display assembly 66.

Figure 9:
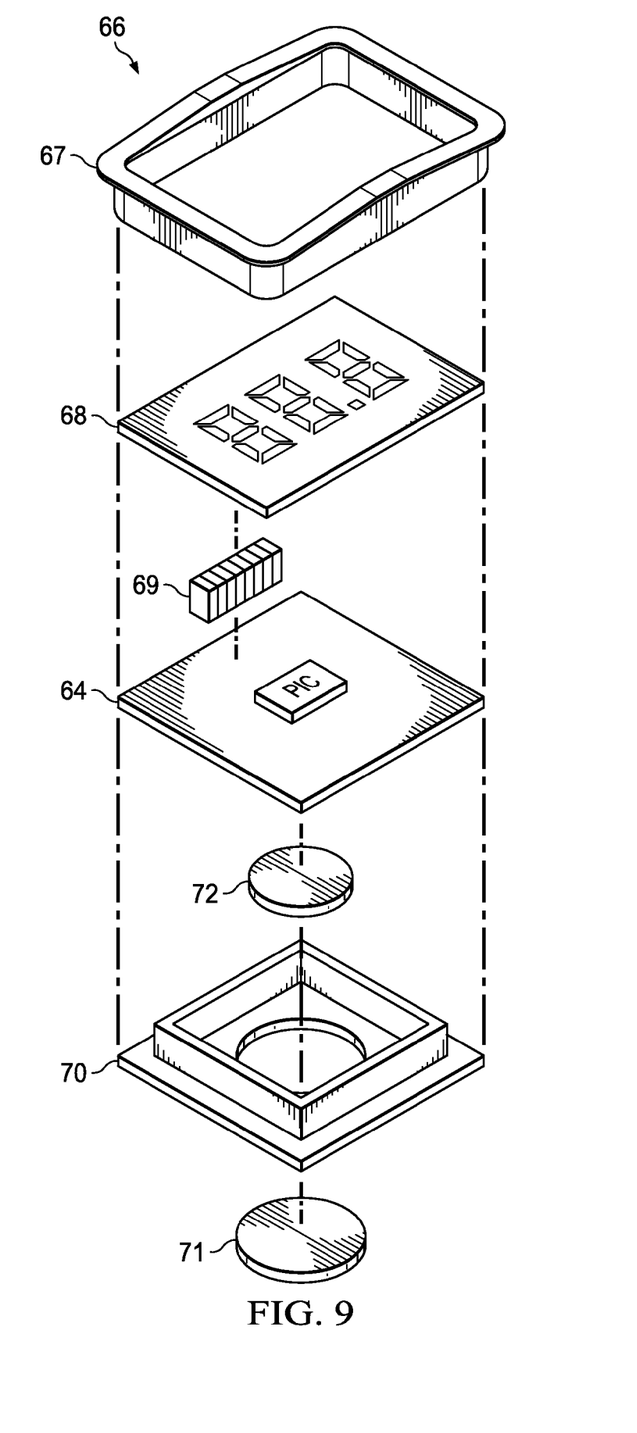
FIG. 9 is an exploded view of a display assembly of the device of FIG. 1.
Figure 10A:
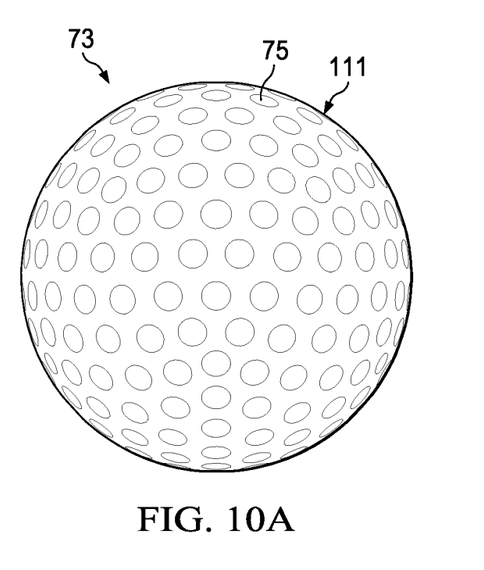
FIG. 10 shows a comparison between two golf balls having different sizes and different configurations of dimples.
Figure 10B:
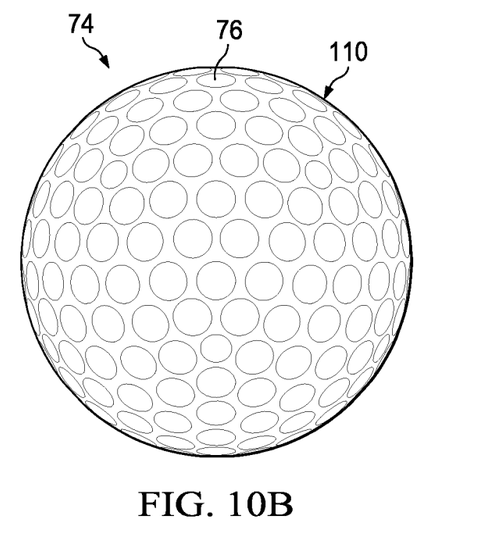

Because anvils 20 and 36 define depressions 26 and 42, respectively, different golf ball types may be accommodated. For example, FIG. 9 shows two different golf balls 73 and 74 having two different size dimples, 75 and 76. Additionally, space between the dimples is smaller for ball 73. Further, golf ball dimple variations exist when balls are made with more than one size of dimple on the same ball. The purpose of depressions 26 and 42 is to form a "dimple negation" feature.

Depressions 26 (FIG. 5) and 42 (FIG. 4), both have diameters 27 and 43, respectfully. The diameters 27 and 43 are larger than dimples 75, 76 of golf balls 73, 74. Preferably, depressions, 26 and 42, are curved to match the radius of a standard golf ball, i.e., a diameter of 1.680±0.15 inches (42.67 mm) for cradling the ball on at least three points of contact on anvils 20, 36, no matter how the ball is placed between anvils 20, 36. The uncertainty of the measurements of force when flat anvils are used to do the same compression test is negated by dimple negation achieved by providing depressions 26, 42 with diameters of 27 and 43 that are larger than the worst case dimple size of a standard golf ball. The dimple negation feature increases the accuracy of measuring the compression rating of a standard golf ball by decreasing the uncertainty of force required to overcome the dimples in the standard golf ball. Dimple negation also allows for less force to be applied against ball 16 to make a measurement of spring rate or by decreasing the uncertainty of the force measurement during an application of low forces.

Dimple negation allows for a lower force and increase in accuracy that will not affect the roundness of the ball after testing for spring rate. Golf balls take time to return to their original roundness after being struck by a club or pinched by a compression testing device. Therefore, a lower applied force is desirable. Dimple negation also allows for less effort needed to turn handle 58 to raise lower anvil 36 against ball 16 to compress ball 16 against upper anvil 20 to an amount of force necessary to successfully measure spring rate, i.e., to achieve an amount of force "F1", as will be explained below.

Figure 7:
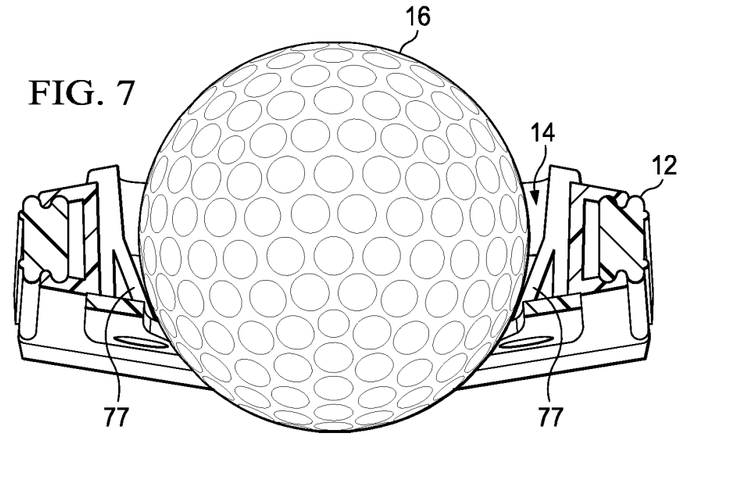
FIG. 7 is a cross-sectional isometric view of the device of FIG. 1 taken along lines 7-7 of FIG. 1 showing one embodiment of a golf ball guide that stops the ball in the correct location for centering the ball within anvils for testing.

To further increase accuracy and repeatability of the compression test, ball 16 must be accurately placed between anvils 20 and 36. Taper stops 77, shown in FIG. 7, function to stop ball 16 in the geometric center between the anvils 20 and 36.

In use, golf ball 16 is placed into ball receiving receptacle 14 of device 10. Taper stops 77 provide a backstop for correctly locating ball 16 between anvils 20 and 36. Golf ball 16 is secured within the ball receiving receptacle 14 and the force gauge assembly 18 by rotating handle 58. Rotation of handle 58 rotates threaded rod 50, which axially displaces lower anvil 36 until golf ball 16 makes contact with upper ball receiving surface 24 of upper anvil 20. Handle 58 should continue to be rotated until golf ball 16 is secured between upper ball receiving surface 24 of upper anvil 20 and lower ball receiving surface 40 of lower anvil 36.

Figure 8:
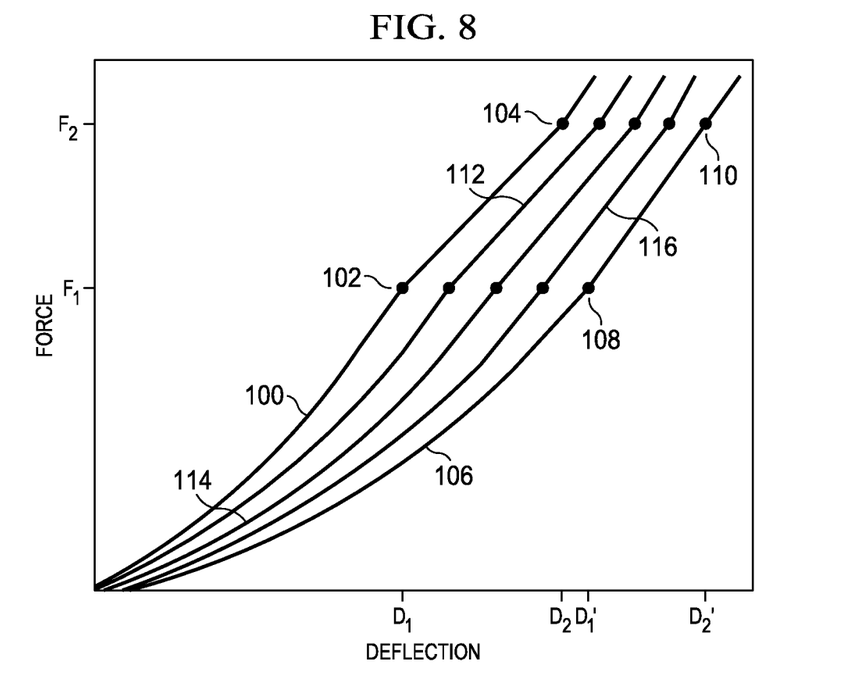
FIG. 8 is a graphical representation of force v. deflection data generated during testing to determining spring rate of golf balls.

Device 10 may be turned on via an activation switch 65 or device 10 may be activated by sensing a low force limit, e.g., force F1 of FIG. 8. Once device 10 is turned on, an encoder count of encoder wheel 62 is communicated to processor 64. At this time, golf ball 16 is compressed by continuing to rotate handle 58 in a first direction to continue to rotate threaded rod 50 for continued axial displacement of lower anvil 36 in an upward direction. The axial displacement of lower anvil 36 produces a corresponding deflection of golf ball 16.

The axial displacement of lower anvil 36 and the corresponding deflection of golf ball 16 is calculated by counting a number of rotations of threaded rod 50 with encoder wheel 62. With the known thread pitch of threaded rod 50 and the known number of rotations of threaded rod 50, axial displacement and golf ball deflection may be measured by encoding the rotation of threaded rod 50. Alternatively, deflection may be calculated by deflection gauge 63 (FIG. 3).

Figure 5:
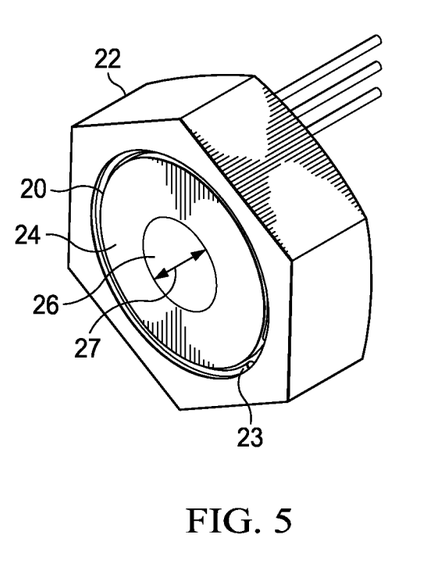
FIG. 5 is an isometric view of the force sensing assembly of the device of FIG. 1.
Figure 6:
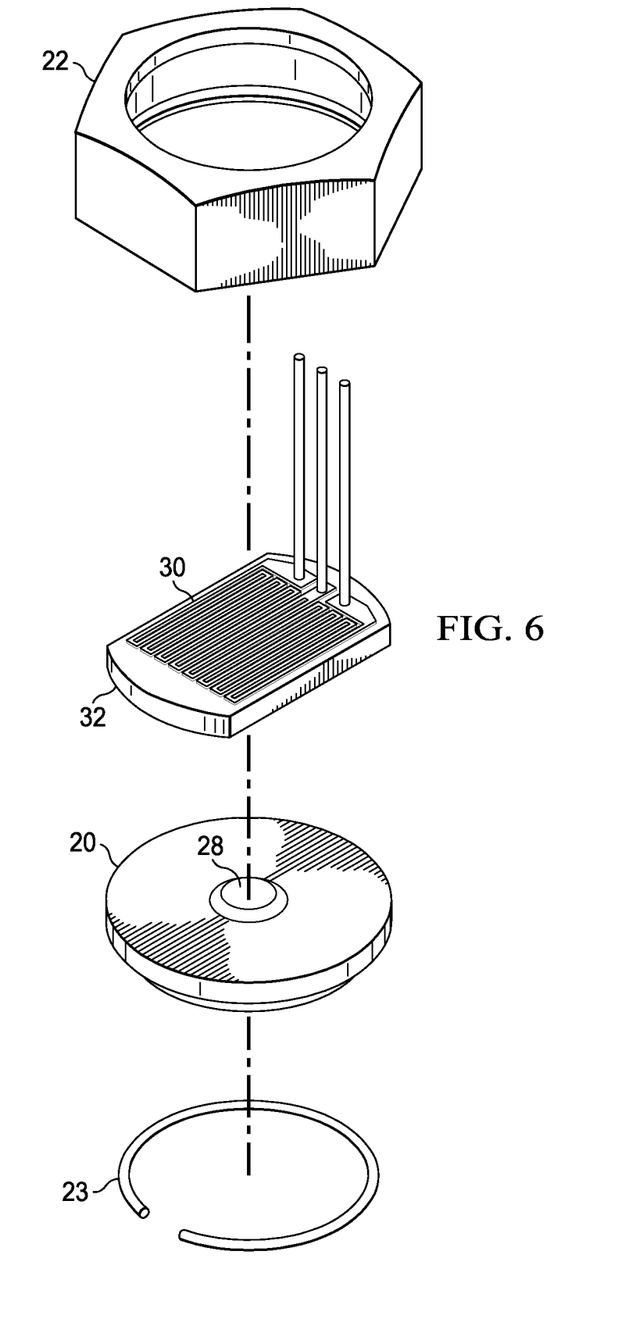
FIG. 6 is an isometric view of the force sensing assembly of the device of FIG. 1 showing an exploded view of the parts within.
Figure 11:
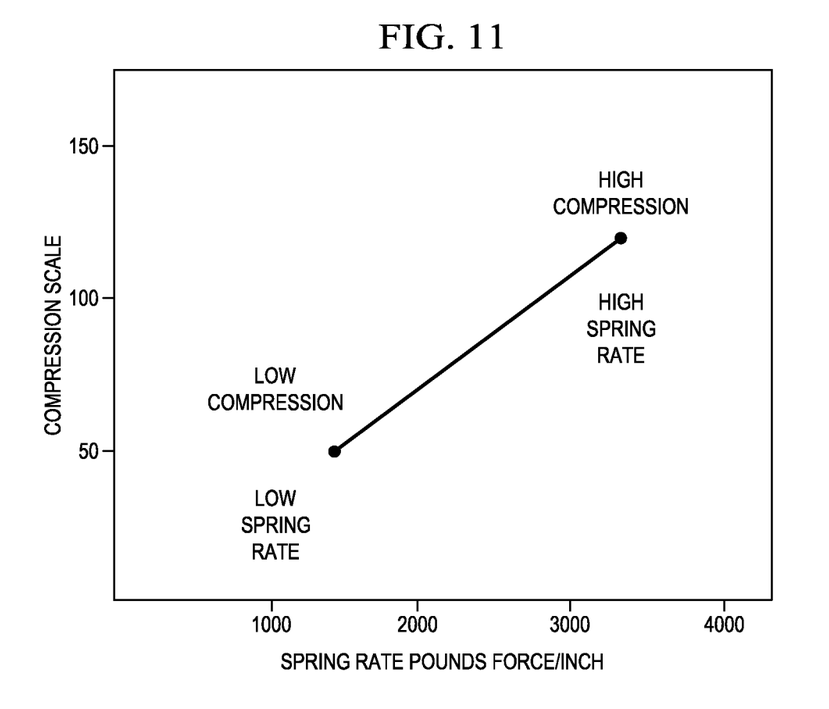
FIG. 11 is a graphical representation that shows correlation between a compression scale and a measured spring rate.

As best shown in FIG. 5, due to an upward force provided by lower anvil 36, upper anvil 20 is additionally displaced such that upwardly facing protuberance 28 of upper anvil 20 contacts beam 30 of tension measuring device 32. Additional compression of golf ball 16 provided by further rotations of handle 58 results in a deflection of beam 30. Tension measuring device 32 determines a force applied by upwardly facing protuberance 28 against beam 30. The force measurement, or load information, of tension measuring device 32 is then communicated to processor 64. Once a force measurement of at least F2 is communicated to processor 64, processor 64 then calculates a spring rate of golf ball 16 by dividing the force calculation by the deflection of golf ball 16. The spring rate of golf ball 16 is then converted by processor 64 to a compression scale value in accordance with the graph of FIG. 11. The compression scale value is then displayed on display screen 66, which alerts a user that further compression, i.e., further rotation of handle 58, is not required. Encoder wheel 62 or deflection gauge 63 is read to determine if lower anvil 36 is lowered after a period of time, e.g., after 5 seconds. If lower anvil 36 is not reduced, then a user is alerted that the golf ball should be removed, e.g., by flashing display 68 or by other warnings.

Handle 58 may then be rotated in a second direction to lower the lower anvil 36, thereby eliminating the compression forces on golf ball 16. Golf ball 16 may then be removed from ball receiving receptacle 14 of device 10. Processor 64 is preferably shut down after a period of non-use, e.g., after 30 seconds.

By using the methods described above, a spring rate and compression scale value may be obtained for a golf ball 16 placed in the ball receiving receptacle 14. Referring now to FIG. 8, shown is a graphical representation of the force v. deflection data from measurements conducted by device 10 of the invention. The x-axis represents a deflection value of golf ball 16. The y-axis indicates a force value delivered by device 10 to create deflection of ball 16. High force/deflection curve 100 indicates a spring rate of a golf ball having a high compression scale value. High force/deflection curve 100 is calculated by measuring a first force (F1) required to achieve a first ball deflection (D1) and plotting point 102. A higher, second force (F2), required to achieve a second ball deflection (D2) is measured and plotted as point 104. Other data points at deflections between D1 and D2 may also be measured and plotted. An example spring rate of a golf ball having a high compression scale value is the change in force divided by the change in deflection, i.e., $$\text{Spring Rate}=(F2-F1)/(D2-D1)$$

Still referring to FIG. 8, low force/deflection curve 106 indicates a spring rate of a golf ball having a relatively low compression scale value. Curve 106 is calculated by measuring a first force (F1) required to achieve a first ball deflection (D1') and plotting point 108. A higher, second force (F2) required to achieve a second ball deflection (D2') is measured and plotted as point 110. An example spring rate of a golf ball having a low compression scale value is the change in force divided by the change in deflection, i.e., $$\text{Spring Rate}=(F2-F1)/(D2'-D1')$$

The calculated spring rate is converted to a compression scale value in software in the processor 64. The calculated compression scale value is then displayed on display screen 66.

The measurement of additional balls having a spring rate between the spring rate of a golf ball having a high compression scale value and a golf ball having a low compression scale value will generate additional force/deflection curves, e.g., curves 112, 114 and 116. In all cases, a low application of force, i.e., F1, and a high application of force, i.e., F2, are applied. The additional force/deflection curves, e.g., curves 112, 114 and 116, are bounded by high compression curve 100 and low compression curve 106. Therefore, accurate determination of the spring rate is dependent upon taking deflection measurements between deflections D1 and D1' at force F1 and is dependent upon taking deflection measurements between deflections D2 and D2' at force F2.

Force/deflection curves 112, 114, and 116 are generated by measuring ball deflection at various compression forces of golf balls having mid-range compression rates. Lines 100, 112, 116 and 106 are substantially parallel to one another within the selected force measurement range of F1 to F2. Therefore, measurements taken with the selected force measurement range of F1 to F2 provide greater differentiations as compared to measurements taken at lower force ranges, e.g., from 0 to F1. Care should be taken to select an upper force F2 that is less than a force that may permanently change the size of a golf ball. In one embodiment, a mechanical step is provided for preventing an application of force that is greater than 200 lbs. Typically, force F2 is approximately twice the magnitude of force F1. In a preferred embodiment, F1 has a value of 10 lbs. and F2 has a value of 130 lbs., although other values may also be used.

The device of the invention is, therefore, useful for providing an ability to measure a spring rate of a golf ball and to calculate and display a compression scale value while a golfer is playing a round of golf.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A device for measuring a golf ball comprising:
   a housing defining a ball receiving receptacle for receiving a golf ball;
   an first anvil and a second anvil mounted in said housing for receiving said golf ball therebetween;
   a strain gauge in communication with one of said first anvil and said second anvil;
   a displacer in communication with one of said first anvil and said second anvil;
   wherein said first anvil defines a first ball receiving surface defining a first ball receiving depression and said second anvil defines a second ball receiving surface defining a second ball receiving depression, said ball receiving depressions having a diameter larger than dimples of said golf ball to be measured, said depressions curved to match the radius of a golf ball for cradling the ball for negating measurement effects due to golf ball dimples when measurement of said golf ball is conducted.

2. The device of claim 1 wherein:
   said first ball receiving depression and said second ball receiving depression are larger than said dimples of said golf ball to be measured.

3. The device of claim 1 wherein:
   said strain gauge is engaged by a protuberance defined by one of said first anvil and said second anvil when said golf ball is compressed.

4. The device of claim 1 wherein:
   said displacer is a threaded rod having an end that is axially displaced by rotation of said threaded rod, said threaded rod for axially displacing one of said first anvil and said second anvil for compressing said golf ball.

5. The device of claim 4 wherein:
   said threaded rod defines a threaded end received within internal threads of one of said first anvil and said second anvil.

6. The device of claim 4 further comprising:
   an encoder wheel proximate said threaded rod;
   wherein said threaded rod has a thread pitch, said threaded rod monitored by said encoder wheel for tracking a number of rotations of said threaded rod;
   a processor in communication with said encoder wheel for converting said number of rotations and said thread pitch into axial displacement of one of said first anvil and said second anvil.

7. The device of claim 1 further comprising:
   a handle affixed to said displacer for rotating said displacer to induce axial displacement of one of said first anvil and said second anvil.

8. The device of claim 1 further comprising:
   a display screen in said housing, said display screen in communication with a processor.

9. The device of claim 1 wherein said force gauge is a strain gauge for providing load information as said displacer is advanced.

10. A method of performing a compression test on a golf ball comprising:
    locating a golf ball between a first anvil and a second anvil, said golf ball located in a first depression defined by said first anvil and in a second depression defined by said second anvil, said first depression and said second depression larger than a dimple defined by said golf ball;
    compressing said golf ball by displacing one of said first anvil and said second anvil to produce a deflection of said golf ball;
    determining a change in said displacement of said one of said first anvil and said second anvil;
    determining a change in force delivered to said one of said first anvil and said second anvil due to said step of compressing said golf ball;
    calculating a spring rate of said golf ball by dividing said change in force by said change in displacement;
    converting said spring rate into a compression scale value.

11. The method according to claim 10 further comprising a step of:
    displaying said compression scale value of said golf ball on a display screen.

12. The method according to claim 10 further comprising a step of:
    determining if said displacement of one of said first anvil and said second anvil is maintained for a predetermined period of time;
    issuing a warning to reverse said displacement of said one of said first anvil and said second anvil to avoid damage to said golf ball.

13. The method according to claim 10 further comprising a step of:
    activating said step of determining said displacement by manually engaging a switch.

14. The method according to claim 10 further comprising a step of:
    determining when said force exceeds a lower threshold amount;
    activating said step of determining said displacement in response to said step of determining when said force exceeds said lower threshold amount.

15. The method according to claim 10 wherein said step of determining said displacement of said one of said first anvil and said second anvil comprises the steps of:
    counting a number of rotations of a displacer with an encoder wheel;
    calculating said displacement using said number of rotations and a pitch of threads on said displacer.

16. The method according to claim 10 wherein said step of determining said displacement of said one of said first anvil and said second anvil comprises reading a deflection gauge, said deflection gauge in communication with said processor.

17. A device for measuring a golf ball comprising:
    a housing defining a ball receiving receptacle for receiving a golf ball;
    an first anvil and a second anvil mounted in said housing for receiving said golf ball therebetween;
    a displacer in communication with one of said first anvil and said second anvil for moving one of said first anvil and said second anvil towards another of said first anvil and said second anvil;

a strain gauge adjacent to one of said first anvil and said second anvil for measuring an applied force against said adjacent one of said first anvil and said second anvil;

said first anvil defines a first ball receiving surface defining a first ball receiving depression and said second anvil defines a second ball receiving surface defining a second ball receiving depression, depressions having a diameter larger than dimples of a golf ball to be measured, said depressions curved to match the radius of said golf ball for cradling the ball, said ball receiving depressions for negating measurement effects due to golf ball dimples when measurement of said golf ball is conducted.

18. The device according to claim 17 wherein:

said strain gauge is engaged by a protuberance defined by one of said first anvil and said second anvil when the golf ball is compressed between said first anvil and said second anvil.

19. The device according to claim 17 further comprising:

an encoder proximate said displacer for counting a number of rotations of said displacer;

wherein said displacer is monitored by said encoder;

a processor in communication with said encoder for determining an axial displacement of one of said first anvil and said second anvil.

20. The method of claim 1 wherein:

said first depression and said second depression are curved to match the radius of said golf ball for cradling said golf ball.

\* \* \* \* \*